United States Patent
Dolph et al.

(10) Patent No.: US 9,693,695 B1
(45) Date of Patent: Jul. 4, 2017

(54) DETECTING ORAL TEMPERATURE USING THERMAL CAMERA

(71) Applicant: International Business Machines Corporation, Armonk, NY (US)

(72) Inventors: Blaine H. Dolph, Western Springs, IL (US); Jui-Hsin Lai, White Plains, NY (US); Ching-Yung Lin, Scarsdale, NY (US); David M. Lubensky, Brookfield, CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/274,074

(22) Filed: Sep. 23, 2016

(51) Int. Cl.
*G06K 9/00* (2006.01)
*A61B 5/01* (2006.01)
(Continued)

(52) U.S. Cl.
CPC ........... *A61B 5/015* (2013.01); *A61B 5/0077* (2013.01); *A61B 5/0086* (2013.01); *A61B 5/7278* (2013.01); *G01J 5/0025* (2013.01); *G01J 5/10* (2013.01); *G01K 13/002* (2013.01); *G06K 9/00248* (2013.01); *G06K 9/00302* (2013.01); *G06T 7/0016* (2013.01); *H04N 5/33* (2013.01);
(Continued)

(58) Field of Classification Search
None
See application file for complete search history.

(56) References Cited

U.S. PATENT DOCUMENTS

| 6,198,102 B1 * | 3/2001 | Shepherd | G01N 21/9054 |
| | | | 250/223 B |
| 7,668,401 B2 * | 2/2010 | Marugame | G06T 13/20 |
| | | | 382/128 |

(Continued)

FOREIGN PATENT DOCUMENTS

EP  1530034 A1  5/2005

OTHER PUBLICATIONS

ADC, "How to Take Temperature", http://adctoday.com/learning-center/about-thermometers/how-take-temperature, American Diagnostic Corporation, Accessed on Sep. 22, 2016, 2 pages.
(Continued)

*Primary Examiner* — Iman K Kholdebarin
(74) *Attorney, Agent, or Firm* — Scully, Scott, Murphy & Presser, P.C.; Daniel P. Morris

(57) ABSTRACT

A method, system, and computer product for detecting an oral temperature for a human include capturing a thermal image for a human using a camera, detecting a face region of the human from the thermal image, detecting a mouth region on the face region, comparing a temperature value on the mouth region to a reference temperature value on a first other face region, detecting an open mouth region on the mouth region based on a comparison result of the temperature value on the mouth region to the reference temperature value of the first other face region, determining whether a mouth of the human is open enough for an oral temperature to be detected, and computing the oral temperature based on temperature values on the mouth region and at least one other face region, responsive to the determination of the mouth being open enough for the oral temperature to be detected.

20 Claims, 10 Drawing Sheets

(51) Int. Cl.
 H04N 5/33 (2006.01)
 G06T 7/00 (2017.01)
 A61B 5/00 (2006.01)
 G01K 13/00 (2006.01)
 G01J 5/00 (2006.01)
 G01J 5/10 (2006.01)
 H04N 5/232 (2006.01)

(52) U.S. Cl.
 CPC ... *A61B 2576/02* (2013.01); *G01J 2005/0077* (2013.01); *G06T 2207/10048* (2013.01); *G06T 2207/30004* (2013.01); *G06T 2207/30201* (2013.01); *H04N 5/23293* (2013.01)

(56) References Cited

U.S. PATENT DOCUMENTS

| | | | | |
|---|---|---|---|---|
| 2005/0226307 A1* | 10/2005 | Lussier | ............... | G01J 5/0022 374/131 |
| 2006/0178582 A1* | 8/2006 | Sheu | ............... | A61B 5/015 600/474 |
| 2008/0077019 A1* | 3/2008 | Xiao | ............... | A61B 5/01 600/474 |
| 2015/0265159 A1* | 9/2015 | Lane | ............... | A61B 5/01 600/549 |

OTHER PUBLICATIONS

FLIR, "FLIR One Thermal Imaging Camera Attachment for iOS and Android", http://www.flir.com/flirone/ios-android/, FLIR Systems, Inc., Accessed on Sep. 22, 2016, 12 pages.

Garcia, C., et al., "Convolutional Face Finder: A Neural Architecture for Fast and Robust Face Detection", IEEE Transactions on Pattern Analysis and Machine Intelligence, Nov. 2004, pp. 1408-1423, vol. 26, No. 11.

Viola, P., et al., "Robust Real-time Face Detection", https://www.google.com/url?sa=t&rct=j&q=&esrc=s&source=web&cd=1&ved=0ahUKEwjzia789t7OAhXFHB4KHVL8BhMQFggjMAA&url=http%3A%2F%2Fwww1.cs.columbia.edu%2F~belhumeur%2Fcourses%2Fbiometrics%2F2010%2Fviolajones.ppt&usg=AFQjCNEHSiU5o1fK0T8Q9IUYiB3vv5w8Xg&sig2=3sMwXhLyC84UmeTRd1Ca1A&cad=rja, Accessed on Sep. 22, 2016, School of Informatics, University of Edinburgh, Presented on Feb. 20, 2009, 29 pages.

Wikipedia, "Human Body Temperature", https://en.wikipedia.org/wiki/Human_body_temperature#Measurement_methods, Wikipedia, Last modified on Sep. 21, 2016, Accessed on Sep. 22, 2016, 4 pages.

\* cited by examiner

DETECTING ORAL TEMPERATURE USING THERMAL CAMERA

FIELD

The present disclosure relates to a method for detecting an oral temperature for a patient, and more particularly to, a non-invasive method, system, and computer product for detecting an oral temperature for a patient using a thermal camera.

BACKGROUND

Recently, a home healthcare system has been receiving increasing attention. In such home healthcare system, measurement of a body temperature for a patient helps a medical professional (e.g., doctor) to check a patient's current health state. In such home healthcare system, a body temperature detection device is generally located at a patient's home, and thus may require a patient' frequent manual operation on it. If a patient or a home user of the home body temperature detection device lacks of skill at the operation thereon, there may occur a temperature detection error which may lead the medical professional to making a wrong decision on the patient's health state. On the other hand, many techniques of detecting a body temperature through a face skin or forehead of a patient have been developed, but it is known that a face skin or forehead temperature is prone to be affected by an ambient temperature and an oral temperature provides a relatively accurate body temperature.

Thus, there is a need for an oral temperature detection technique that can be applied to a home healthcare application where a medical professional is remotely located from a patient.

BRIEF SUMMARY

In an aspect of the present disclosure, a computer-implemented method for detecting an oral temperature for a human is provided. The method includes capturing a thermal image for a human using a camera having a thermal image sensor, detecting a face region of the human from the thermal image, detecting a mouth region on the face region, comparing a temperature value on the mouth region to a reference temperature value on a first other face region, detecting an open mouth region on the mouth region based on a comparison result of the temperature value on the mouth region to the reference temperature value of the first other face region, determining whether a mouth of the human is open enough for an oral temperature to be detected, and computing the oral temperature based on temperature values on the mouth region and at least one other face region, responsive to the determination of the mouth being open enough for the oral temperature to be detected.

In an aspect of the present disclosure, a system for detecting an oral temperature for a human is provided. The system includes a memory device storing machine executable program instructions and at least one processing device coupled to the memory device. The at least one processing device is configured to run the machine executable program instructions to perform capturing a thermal image for a human using a camera having a thermal image sensor, detecting a face region of the human from the thermal image, detecting a mouth region on the face region, comparing a temperature value on the mouth region to a reference temperature value on a first other face region, detecting an open mouth region on the mouth region based on a comparison result of the temperature value on the mouth region to the reference temperature value of the first other face region, determining whether a mouth of the human is open enough for an oral temperature to be detected, and computing the oral temperature based on temperature values on the mouth region and at least one other face region, responsive to the determination of the mouth being open enough for the oral temperature to be detected.

In an aspect of the present disclosure, a computer program product stored in a computer-readable storage medium having computer readable program instructions is provided. The computer readable program instructions are read and carried out by a processing device of performing a method for detecting an oral temperature for a human. The method includes capturing a thermal image for a human using a camera having a thermal image sensor, detecting a face region of the human from the thermal image, detecting a mouth region on the face region, comparing a temperature value on the mouth region to a reference temperature value on a first other face region, detecting an open mouth region on the mouth region based on a comparison result of the temperature value on the mouth region to the reference temperature value of the first other face region, determining whether a mouth of the human is open enough for an oral temperature to be detected, and computing the oral temperature based on temperature values on the mouth region and at least one other face region, responsive to the determination of the mouth being open enough for the oral temperature to be detected.

DETAILED DESCRIPTION OF THE EMBODIMENTS

Embodiments of the present invention will now be described in detail on the basis of the drawings. However, the following embodiments do not restrict the invention claimed in the claims. Moreover, all combinations of features described in the embodiments are not necessarily mandatory for the architecture of the present invention. Like numbers are assigned to like elements throughout the description of the embodiments of the present disclosure.

A method, system, and computer product for detecting an oral temperature for an animate object are disclosed. A system for detecting the oral temperature for the animate object is referred to as an "oral temperature detection system". In the present disclosure, an "animate object" may be understood to include, but is not limited to, a human, a patient, or other warm-blood animals (e.g., mammals) under diagnosis.

Figure 1A:
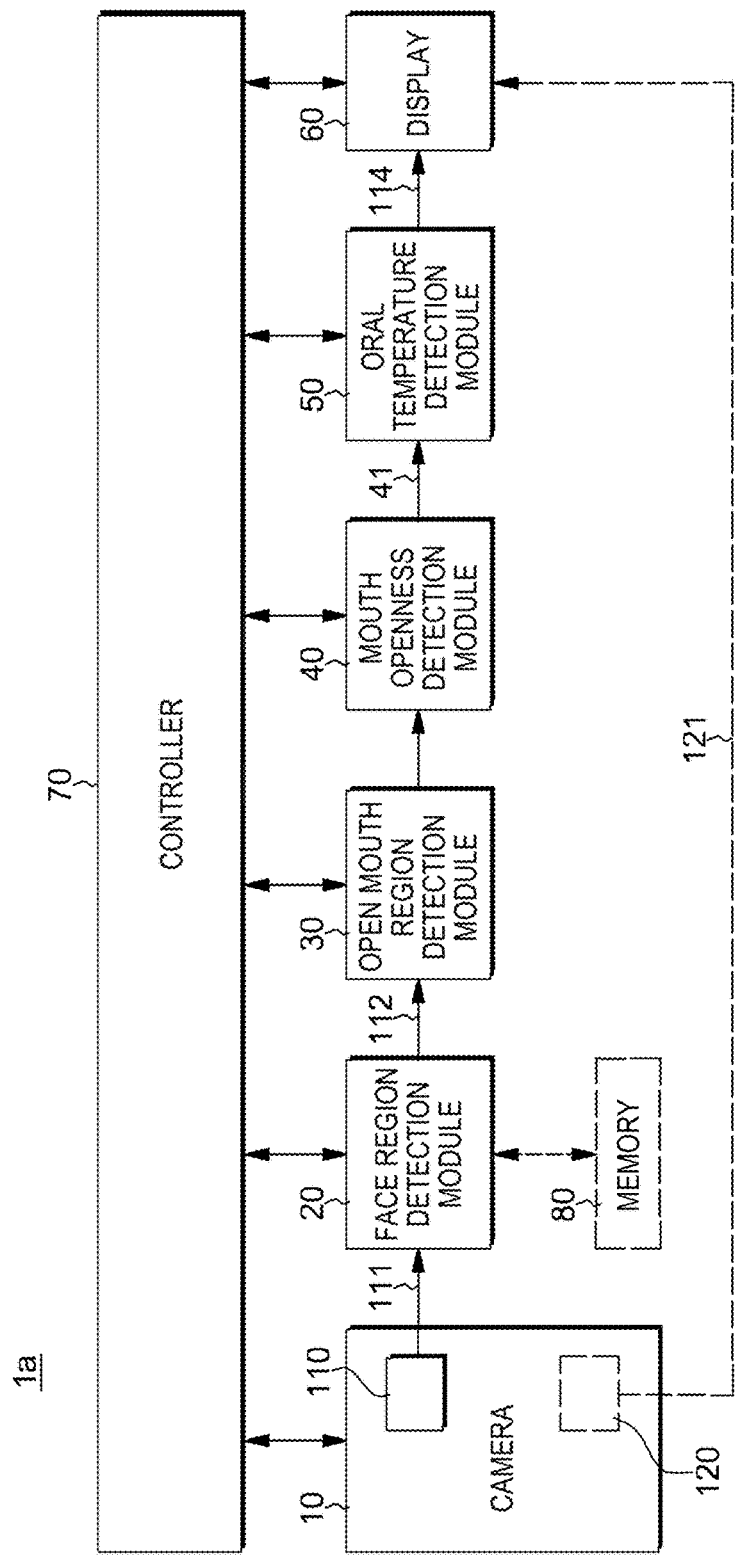
FIG. 1A is a block diagram of an oral temperature detection system according to an exemplary embodiment of the present disclosure.
Figure 1B:
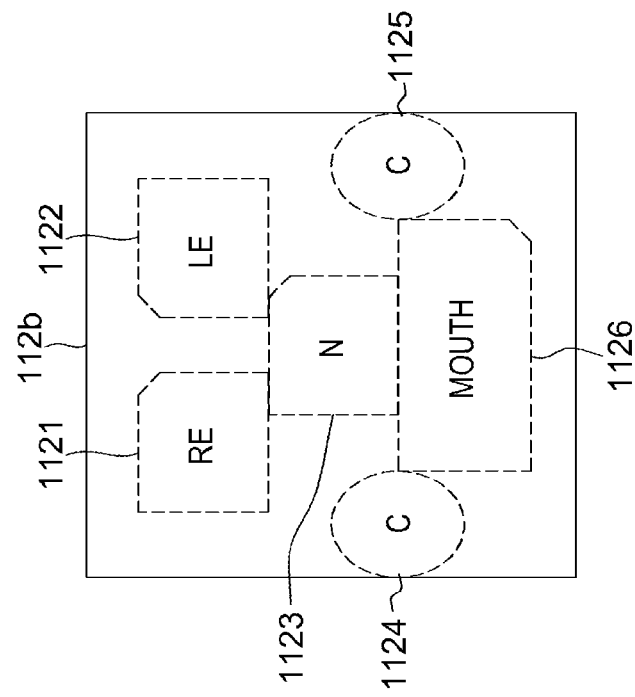
FIGS. 1B and 1C illustrate examples of images captured in the oral temperature detection system of FIG. 1A, according to an exemplary embodiment of the present disclosure.
Figure 1B:
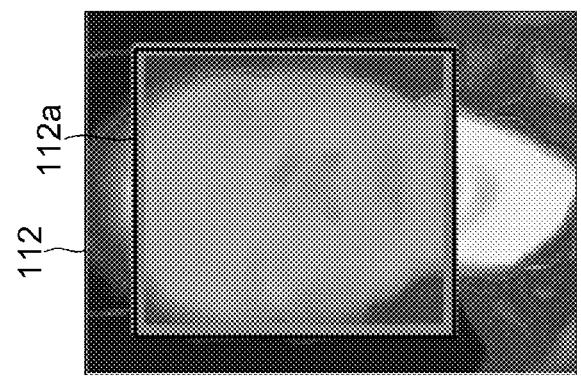
Figure 1B:
Figure 1C:
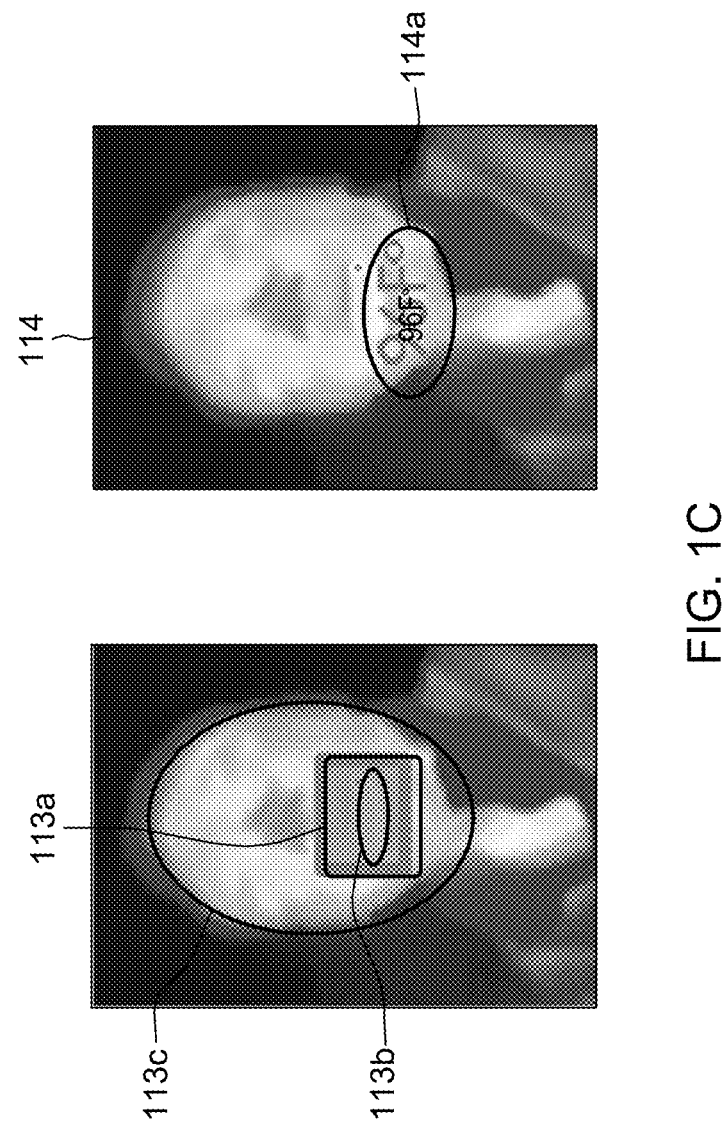

FIG. 1A is a block diagram of an oral temperature detection system 1a according to an exemplary embodiment of the present disclosure. FIGS. 1B and 1C illustrate examples of images captured in the oral temperature detection system 1a of FIG. 1A, according to an exemplary embodiment of the present disclosure.

Referring to FIG. 1A, an oral temperature detection system 1a according to an exemplary embodiment of the present disclosure may include a camera device 10 for capturing a thermal image 111 for an animate object (not shown), a face region detection module 20 for detecting a face region of the animate object from the thermal image 111, an open mouth region detection module 30 for detecting an open mouth region from the detected face region, a mouth openness detection module 40 for detecting a mouth openness from the open mouth region, an oral temperature detection module 50 for detecting (or calculating) an oral temperature of the animate object, a display device 60 for displaying the detected oral temperature, and a controller 70 for controlling operations of the camera device 10, the face region detection module 20, the open mouth region detection module 30, the mouth openness detection module 40, the oral temperature detection module 50, and the display device 60.

The camera device 10 may include a thermal image sensing unit 110 for capturing the thermal image 111 for the animate object. In the context of the present disclosure, the thermal image 111 may be understood as an image including a plurality of thermal image pixels (e.g., pixels of temperature values), each of which represents a corresponding one of temperature values of the image. In one embodiment, the thermal image sensing unit 110 may be implemented based on an infrared (IR) temperature sensing technique. In some embodiments, the camera device 10 may further include an RGB image sensing unit 120 for capturing an RGB image 121 for the animate object. Thus, the camera device 10 may generate the thermal image 111 and/or the RGB image 121. The RGB image 121 may represent an actual image of the animate object, which, as an example, is to be displayed together with a detected oral temperature value (of the animate object) and/or the thermal image 111, to a medical processional (not shown). In one embodiment, the thermal and RGB images 111 and 121 have substantially the same number of pixels and the matrix size as each other.

As shown in FIG. 1A, the face region detection module 20 may receive the thermal image 111 from the camera device 10 and perform a face region detection from the thermal image 111. Empirically, the thermal image 111 may have thermal distribution related to unique features for a human face. Examples of the features for a human face may include, but are limited: 1) a face region may be shown in a thermal image with a higher temperature and denser capillary than other non-facial region such as a background region; 2) an eye region where temperatures around eyes may be higher than other regions such as cheeks, a nose bridge, or the like; 3) a nose region where a temperature on the nose region is close to a background temperature (e.g., ambient temperature); and 4) an eye region has the highest temperature on the face region. These empirical information allow to derive empirical parameters such as each face feature' location, size, thermal indices (e.g., temperature values), or the like, and such empirical parameters may be stored in memory 80 included in the system 1a and incorporated into a face detection model which facilitates a faster and more accurate face region detection.

To avoid computational complexity and speed up a face region detection process, it is well known that a subset of relevant features (e.g., weak classifiers) for a subject image must be chosen rather than all possible features set are chosen. In one embodiment, functions of the face region detection module 20 may be implemented using face region detection techniques well known in the art based on, but are not limited to, an Adaptive Boosting (Adaboost) algorithm (disclosed in a reference entitled "Robust real-time face detection", Paul Viola and Michael Jones, Feb. 20, 2009) and a deep learning algorithm (disclosed in a reference entitled "Convolutional face finder: a neural architecture for fast and robust face detection", Christophe Garcia, IEEE transactions on pattern analysis and machine intelligence, November, 2004). In one example, the Adaboost algorithm is used to choose a subset of relevant features and train a series of strong classifiers. The strong classifiers may be used in a cascaded manner to discriminate non-face regions from the face region. The detailed algorithms and skills for implementation of the face region detection module 20 are well known to those skilled in the art, and are not the main parts of the present disclosure, and thus are not described herein. By way of example only, shown in FIG. 1B is an example thermal image 111 and an example image 112 captured as a result of face region detection being made on the thermal image 111. Within the image 112 of FIG. 1B, a face region 112a is shown. The face region detection module 20 may further be configured to locate face features on the face region 112a and an example of the located face features is shown with a reference number 112b in FIG. 1B. Shown in FIG. 1B are eye regions 1121 and 1122, a nose region 1123, cheek regions 1124 and 1125, and a mouth region 1126. Shown in FIG. 1C is an example captured image 113a for a mouth region.

Referring back to FIG. 1A, the open mouth region detection module 30 may detect an open mouth region on the mouth region 113a (FIG. 1C) provided by the face region detection module 20. To this end, the open mouth region detection module 30 may identify a plurality of thermal image pixels (not shown) on the mouth region 113a and compare a respective temperature value of each thermal image pixel to a reference temperature value T_ref (see equation 1 below). If one or more image pixels on the mouth region 113a have higher temperature values than the reference temperature value T_ref, the open mouth region detection module 30 may determine a region defined by such one or more image pixels as an open mouth region 113b, as exemplary shown in FIG. 1C. In one embodiment, the reference temperature value T_ref may be obtained based on a temperature value of other reference face region (e.g., non-mouth face region) than the mouth region 113a. For example, the reference temperature value T_ref may be a value higher than a temperature value T_otr of the other reference face region (e.g., cheek region 1124 or 1125 of FIG. 1B) by a constant value C, as shown in the following equation (1):

$$T\_ref = T\_otr + C \qquad \text{Equation (1)}$$

In one embodiment, when a cheek region is used as the other reference face region of which temperature value is compared to a corresponding one of the thermal image pixels within the mouth region 113a for detecting an open mouth region 113b, the constant value C may range from 1.5 to 5.0 degrees Celsius. Stated differently, a region on the mouth region 113a with one or more thermal pixels having higher temperature values by a temperature value C may be determined as an open mouth region 113b.

Referring still to FIG. 1A, the mouth openness detection module 40 may detect a mouth openness. Stated differently, the mouth openness detection module 40 may determine whether a mouth of an animate object is open enough such that an oral temperature for the animate object can be detected. For example, if a mouth of the animate object is open larger than a predetermined value, the mouth openness detection module 40 may determine that the mouth is open enough and an oral temperature is ready to be detected; otherwise, the mouth openness detection module 40 may determine that the mouth is not clearly open enough or the mouth is closed.

To determine the mouth openness, in some embodiments, the mouth openness detection module 40 may identify an open mouth region 113b (FIG. 1C) on the mouth region 113a (FIG. 1C), compare a size of the open mouth region 113b to a size of the entire face region 113c (FIG. 1C), and determine a ratio of the size of the open mouth region 113b to the size of the entire face region 113c. When the ratio of the size of the opened mouth region 113b to the size of the entire face region 113c is equal to or greater than a reference ratio that ranges, e.g., from $1/17$ to $1/10$, the mouth openness detection module 40 may determine that the mouth is open enough for an oral temperature to be detected; otherwise determine that the mouth is not clearly open or closed. In comparing the sizes between the open mouth region 113b and the entire face region 113c, the number of thermal image pixels in each of the open mouth region 113b and the entire face region 113c may be used. For example, the number of thermal image pixels in the open mouth region 113b may be calculated as correspondingly to the size of the open mouth region 113b, and the number of thermal image pixels in the face region 113c may be calculated as correspondingly to the size of the face region 113c.

By way of example only, if $1/17$ is selected as the reference ratio to be compared to the ratio of the size of the opened mouth region 113b to the size of the entire face region 113c, and the open mouth region 113b and the face region 113c are defined respectively in 10×10 (pixel-width×pixel-height) and 40×40 (pixel-width×pixel-height), the mouth openness detection module 40 may determine a size of the open mouth region 113b as 100 pixel region and a size of the face region 113c as 1600 pixel region. In this case, the ratio of the size (i.e., 100 pixel region) of the open mouth region 113b to the size (i.e., 1600 pixel region) of the face region 113c may be $1/16$ which is greater than $1/17$, the reference ratio. Thus, the mouth openness detection module 40 may determine that a mouth is open enough for an oral temperature to be detected and generate a trigger signal 41 that indicates that a mouth is open.

Referring still to FIG. 1A, the oral temperature detection module 50 may calculate an oral temperature for an animate object responsive to receipt of the trigger signal 41, based on the following equation.

$$T\_oral = T\max\_m + \alpha * (T\max\_e - T\max\_n) \quad \text{Equation (2)}$$

Here, Tmax_m, Tmax_e, and Tmax_n represent maximum temperatures (e.g., degrees Celsius) on respective mouth region, eye region, and nose region, and α is a scaling parameter (e.g., 0.5). "*" indicates a multiplication operation. Shown in FIG. 1C is an example image 114 and an oral temperature value 114a (e.g., 96 degrees Fahrenheit) captured when the oral temperature is detected (or calculated) for the animate object.

Referring still to FIG. 1A, the display device 60 may display the detected oral temperature value T_oral together with the thermal image 111 (see 114 of FIG. 1C). In some embodiments, although not shown, the display device 60 may display the detected oral temperature value T_oral together with the thermal image 111 and the RGB image 121 of the animate object.

In some embodiments, at least one of the face region detection module 20, the open mouth region detection 30, the mouth openness detection module 40, and the oral temperature detection module 50 may be implemented by a hardware processor (not shown) or based on a (field-programmable gate array) FPGA design (not shown), but in another embodiment, implemented based on program codes which are stored in memory (not shown) or in a hardware processor and executed by the hardware processor.

Figure 2A:
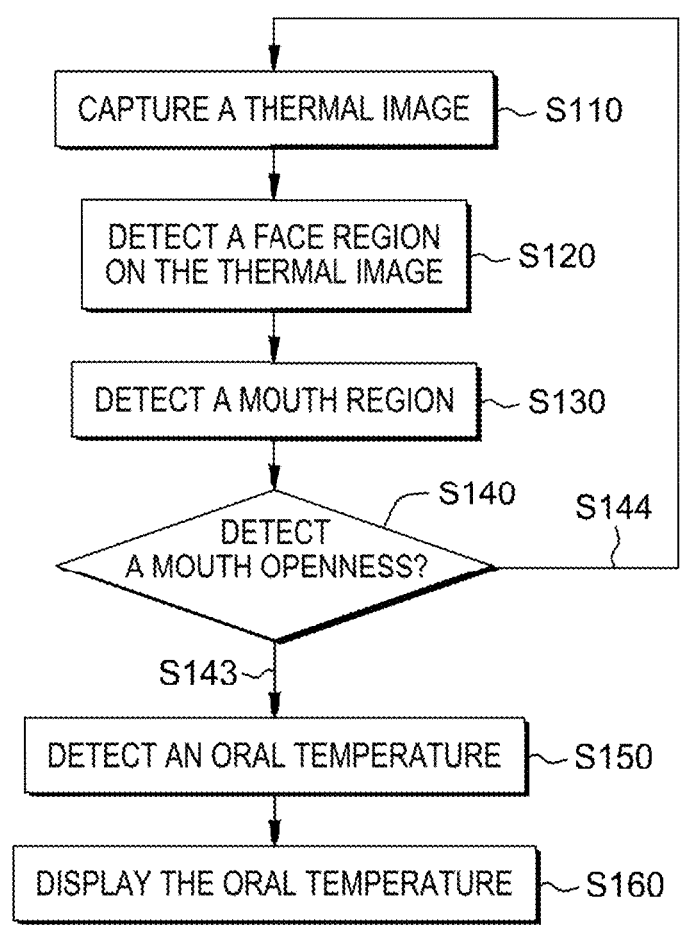
FIGS. 2A to 2D are flow charts illustrating a method for detecting an oral temperature for an animate object according to an exemplary embodiment of the present disclosure.

FIGS. 2A to 2D are flow charts illustrating a method for detecting an oral temperature for an animate object according to an exemplary embodiment of the present disclosure. As shown in FIG. 2A, the method according to an embodiment of the present disclosure may include capturing a thermal image (111 of FIG. 1A) and/or an RGB image (e.g., 121 of FIG. 1A) for an animate object using a camera device (10 of FIG. 1A) in an operation of step S110. The camera device 10 may capture an image for the animate object.

Figure 2B:
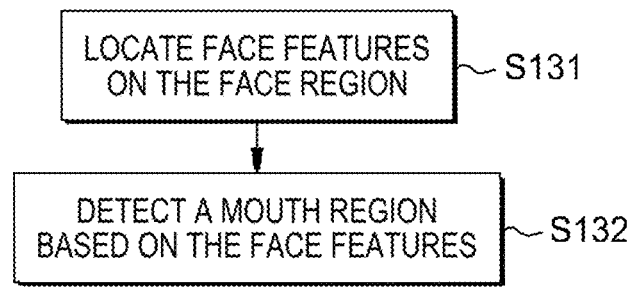

In addition, as shown in FIG. 2A, in step S120, a face region may be detected from the thermal image captured through the step S110. In one embodiment, if the face region is not successfully detected, the capturing of an image for an animate object (S110) may be repeated (not shown). Next, in step S130, a mouth region may be detected on the face region detected through the step S120. As shown in FIG. 2B, the mouth region may be detected by locating face features on the face region (S131) and detecting the mouth region based on the face features (S132).

Next, referring back to FIG. 2A, a mouth openness may be detected (S140). Stated differently, it is determined whether a mouth is open enough for an oral temperature to be detected. If the mouth is determined to be open (S143), an oral temperature may be detected (or calculated) on the open mouth region (S150); otherwise (S144), the steps S110, S120, S130, and S140 may be repeated until the mouth is determined to be open.

Figure 2C:
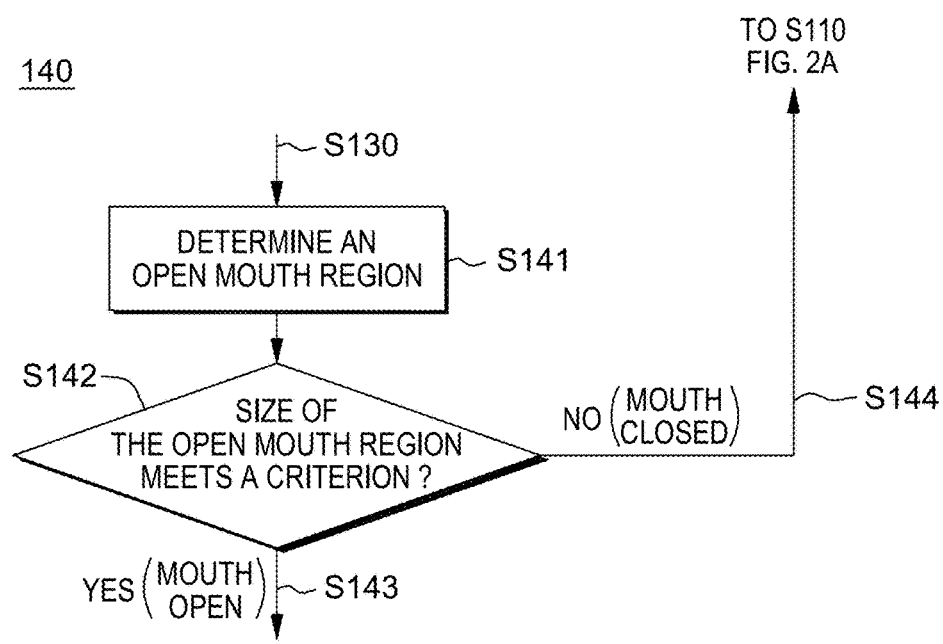
Figure 2D:
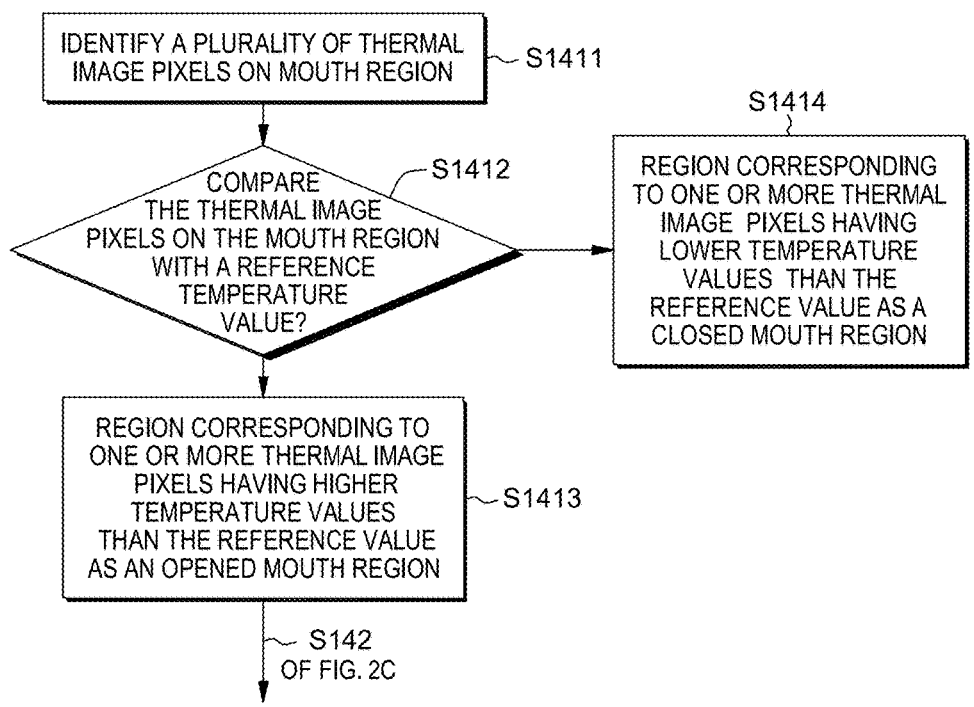

As shown in FIG. 2C, the determining of whether a mouth is open enough for an oral temperature to be detected (step S140) may further include determining an open mouth region on the mouth region (S141). To this end, as shown in FIG. 2D, a plurality of thermal image pixels corresponding to the mouth region may be identified (S1411) and a respective temperature value of each thermal image pixel may be compared to a reference temperature value (S1412). When one or more image pixels on the mouth region have higher temperature values than the reference temperature value (e.g., T_ref in Equation (1)), a region defined by such one or more image pixels may be detected as an open mouth region (S1413); otherwise, such region may be determined as a closed mouth region (S1414). Next, referring back to FIG. 2C, a size (or area) of the open mouth region may be compared to a size (or area) of the entire face region in step S142. When a mouth is open larger than a predetermined value (YES), it may be determined that the mouth is open enough and an oral temperature is ready to be detected (S143); otherwise (NO), it may be determined that the mouth is not clearly open or the mouth is closed (S144) and the steps S110, S120, S130, and S140 may be repeated until the mouth is determined to be open. In some embodiments, a ratio of the size of the open mouth region to the size of the entire face region may be determined. When the ratio of the size of the open mouth region to the size of the entire face region is equal to or greater than a reference ratio that ranges, e.g., from $1/17$ to $1/10$, it may be determined that the mouth is open for an oral temperature to be detected; otherwise it may be determined that the mouth is not clearly open enough or closed. In comparing the sizes between the open mouth region and the entire face region, the number of thermal image pixels in each of the open mouth region and the entire face region may be used. For example, the number of thermal image pixels in the open mouth region may be calculated as correspondingly to the size of the open mouth region, and the number of thermal image pixels in the face region may be calculated as correspondingly to the size of the face region.

In the step S150, an oral temperature for an animate object may be calculated using the above-mentioned Equation (2). Next, in step S160, the calculated oral temperature may be displayed using a display device (e.g., 60 of FIG. 1A).

Figure 3:
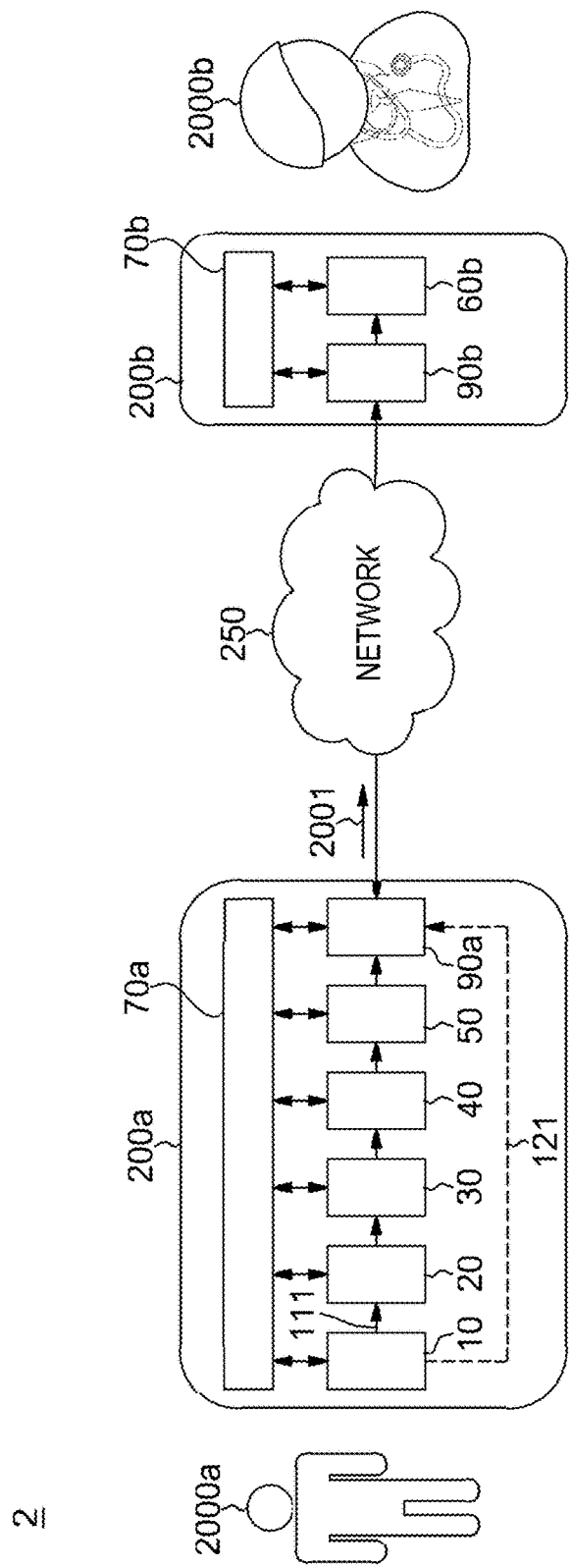
FIG. 3 illustrates a schematic of an example home healthcare network system where a face region detection module, an open mouth region detection module, a mouth openness detection module, and an oral temperature detection module are implemented in a communication device at a patient's site, according to an exemplary embodiment of the present disclosure.

FIG. 3 illustrates a schematic of an example home healthcare network system 2 where a face region detection module, an open mouth region detection module, a mouth openness detection module, and an oral temperature detection module are implemented in a communication device at a patient's site remote from a medical professional, according to an exemplary embodiment of the present disclosure.

Referring to FIG. 3, a patient 2000a and a medical professional (e.g., doctor) 2000b may be located at a distance and connected through a communication network 250. For communication over the network 250, each of the patient 2000a and the medial professional 2000b uses at least one communication device. For illustrative purpose, as shown, a communication device 200a may be located at the patient 2000a's site and a communication device 200b may be located at the medical professional 2000b's site. Stated differently, the communication device 200a may be associated with the patient 2000a and the communication device 200b may be associated with the medical professional 2000b remotely located from the patient 2000a.

As shown, the communication device 200a located at the patient 2000a' site may include a camera device 10 for capturing a thermal image 111 for the patient 2000a, a face region detection module 20 for detecting a face region of the patient 2000a from the thermal image 111, an open mouth region detection module 30 for detecting an open mouth region on the detected face region, a mouth openness detection module 40 for determining whether the patient 2000a's mouth is open enough for an oral temperature to be detected, and an oral temperature detection module 50 for detecting (or calculating) an oral temperature for the patient 2000a on the open mouth region. Detailed operations or configurations of the camera device 10, the face region detection module 20, the open mouth region detection module 30, the mouth openness detection module 40, and the oral temperature detection module 50 may be substantially the same as those of FIG. 1A. Duplicate descriptions thereof will be omitted for the sake of simplicity. The communication device 200a may further include a network adaptor 90a for sending/receiving data to/from the communication device 200b located at the medical professional 2000b's site over the communication network 250; in some embodiments, the communication device 200a may be configured to send a data signal 2001, which includes an oral temperature value detected by the oral temperature detection module 50, to the communication device 200b using the network adaptor 90a. The communication device 200a may further include a controller 70a for controlling operations of the camera device 10, the face region detection module 20, the open mouth region detection module 30, the mouth openness detection module 40, and the oral temperature detection module 50. Thus, the communication device 200b located at the medical professional 2000b's may receive the data signal 2001 using a network adaptor 90b included therein and display the oral temperature value of the patient 2000a using a display device 60b included therein. In another embodiment, the camera device 10 of the communication device 200a may further capture an RGB image 121 for the patient 2000a and provide the RGB image 121 to the network adaptor 90a, and thus, the data signal 2001 may further include the RGB image 121 as well as the thermal image 111 and the oral temperature value detected by the oral temperature detection module 50. Thus, at least one of the RGB image 121, the thermal image 111, and the oral temperature for the patient 2000a or any combination(s) thereof may be displayed using the display device 60b. The communication device 200b may further include, but is not limited to, a controller 70b for controlling the operations of the network adaptor 90b and the display device 60b.

Referring to FIG. 3, each of the communication devices 200a and 200b may be implemented with a ultra-mobile personal computer (UMPC), a net-book, a personal digital assistance (PDA), a portable computer (PC), a web tablet, a wireless phone, a mobile phone, a smart phone, an e-book, a portable multimedia player (PMP), a portable game console, a navigation device, a black box, a digital camera, a digital multimedia broadcasting (DMB) player, a digital audio recorder, a digital audio player, a digital picture recorder, a digital picture player, a digital video recorder, a digital video player, or the like.

Further, although the camera device 10 is illustrated to be included in the communication device 200a, it may be embodied in the communication device 200a or a peripheral device thereto.

The network 250 may include wired communications based on Internet, local area network (LAN), wide area network (WAN), or the like, or wireless communications based on code division multiple access (CDMA), global system for mobile communication (GSM), wideband CDMA, CDMA-2000, time division multiple access (TDMA), long term evolution (LTE), wireless LAN, Bluetooth, or the like.

Figure 4:
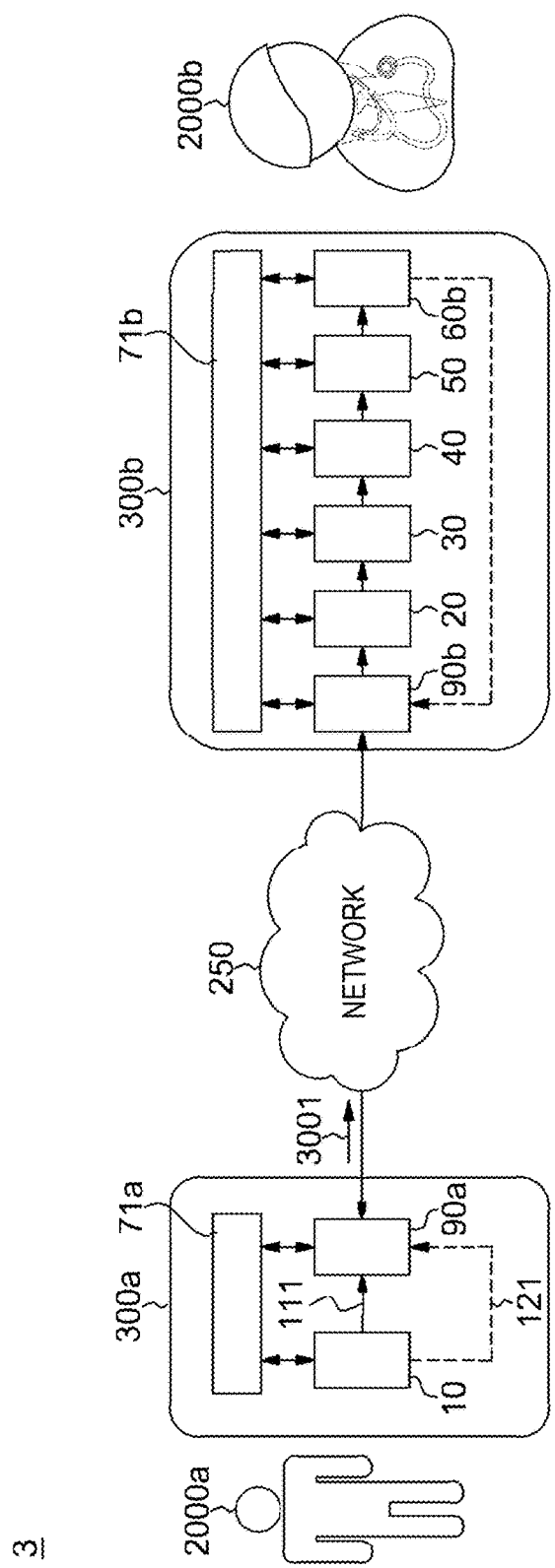
FIG. 4 illustrates a schematic of an example home healthcare network system where a face region detection module, an open mouth region detection module, a mouth openness detection module, and an oral temperature detection module are implemented in a communication device located at a medical professional's site, according to an exemplary embodiment of the present disclosure.

FIG. 4 illustrates a schematic of an example home healthcare network system 3 where a face region detection module, an open mouth region detection module, a mouth openness detection module, and an oral temperature detection module are implemented in a communication device located at a medical professional site remote from a medical professional, according to an exemplary embodiment of the present disclosure.

Referring to FIG. 4, a patient 2000a and a medical professional 2000b may be located at a distance and connected through a communication network 250. For communication over the network 250, each of the patient 2000a and the medial professional 2000b uses at least one communication device. For illustrative purpose, as shown, a communication device 300a may be located at the patient 2000a's site and a communication device 300b may be located at the medical professional 2000b's site. Stated differently, the communication device 300*a* may be associated with the patient 2000*a* and the communication device 300*b* may be associated with the medical professional 2000*b* remotely located from the patient 2000*a*.

As shown, the communication device 300*a* located at the patient 2000*a*' site may include, but is not limited to, a camera device 10, a network adaptor 90*a*, and a controller 71*a* for controlling operations of the camera device 10 and the network adaptor 90*a*. The camera device 10 may capture a thermal image 111 for the patient 2000*a* and send the captured thermal image 111 to a network adaptor 90*a*. The network adaptor 90*a* may be configured to send/receive data to/from the communication device 300*b* at the medical professional 2000*b*'s site, over the communication network 250; in some embodiments, the communication device 300*a* may be configured to send a data signal 3001, which includes the thermal image 111 for the patient 2000*a*, to the communication device 300*b* using the network adaptor 90*a*. Thus, the communication device 300*b* located at the medical professional 2000*b*'s site may receive the thermal image 111 of the data signal 3001 using a network adaptor 90*b* included therein. The communication device 300*b* may include a face region detection module 20 for detecting a face region of the patient 2000*a* from the thermal image 111 received from the communication device 300*a*, an open mouth region detection module 30 for detecting an open mouth region on the detected face region, a mouth openness detection module 40 for determining whether the patient 2000*a*'s mouth is open enough for an oral temperature to be detected, and an oral temperature detection module 50 for detecting (or calculating) an oral temperature for the patient 2000*a* on the open mouth region. Detailed operations or configurations of the face region detection module 20, the open mouth region detection module 30, the mouth openness detection module 40, and the oral temperature detection module 50 may be substantially the same as those of FIG. 1A. Duplicate descriptions thereof will be omitted for the sake of simplicity. Next, the communication device 300*b* may display the oral temperature value detected by the oral temperature detection module 50 using the display device 60*b* included therein. The communication device 300*b* may further include a controller 71*b* for controlling operations of the network adaptor 90*b*, the face region detection module 20, the open mouth region detection module 30, the mouth openness detection module 40, the oral temperature detection module 50, and the display device 60*b*. In another embodiment, the camera device 10 of the communication device 300*a* may further capture an RGB image 121 for the patient 2000*a* and provide the RGB image 121 to the network adaptor 90*a*, and thus, the data signal 3001 to be transferred to the communication device 300*b* may further include the RGB image 121 as well as the thermal image 111. Thus, the communication device 300*b* may receive the RGB image 121 and/or the thermal image 111, detect (or calculate) an oral temperature based on the thermal image 111, and display at least one of the RGB image 121 and/or the thermal image 111, and the oral temperature or any combination(s) thereof using the display device 60*b*.

Referring still to FIG. 4, each of the communication devices 300*a* and 300*b* may be implemented with an UMPC, a net-book, a PDA, a PC, a web tablet, a wireless phone, a mobile phone, a smart phone, an e-book, a PMP, a portable game console, a navigation device, a black box, a digital camera, a DMB player, a digital audio recorder, a digital audio player, a digital picture recorder, a digital picture player, a digital video recorder, a digital video player, or the like.

Further, although the camera device 10 is illustrated to be included in the communication device 300*a*, it may be embodied in the communication device 300*a* or a peripheral device thereto.

The home healthcare network system 2 or 3 using an oral temperature detection system according to an embodiment of the present disclosure does not require a patient or home user to manipulate or operate the temperature detection system, other than to take the thermal and/or RGB images, which may cause a temperature detection error, instead facilitating a real-time oral temperature detection while a medical professional and a patient are being on a conversation (or in communication), it may minimize the temperature detection error due to the patient's or home user's immature operating skill on a device and thus allow a medical professional to monitor a patient's health state in real-time.

Figure 5:
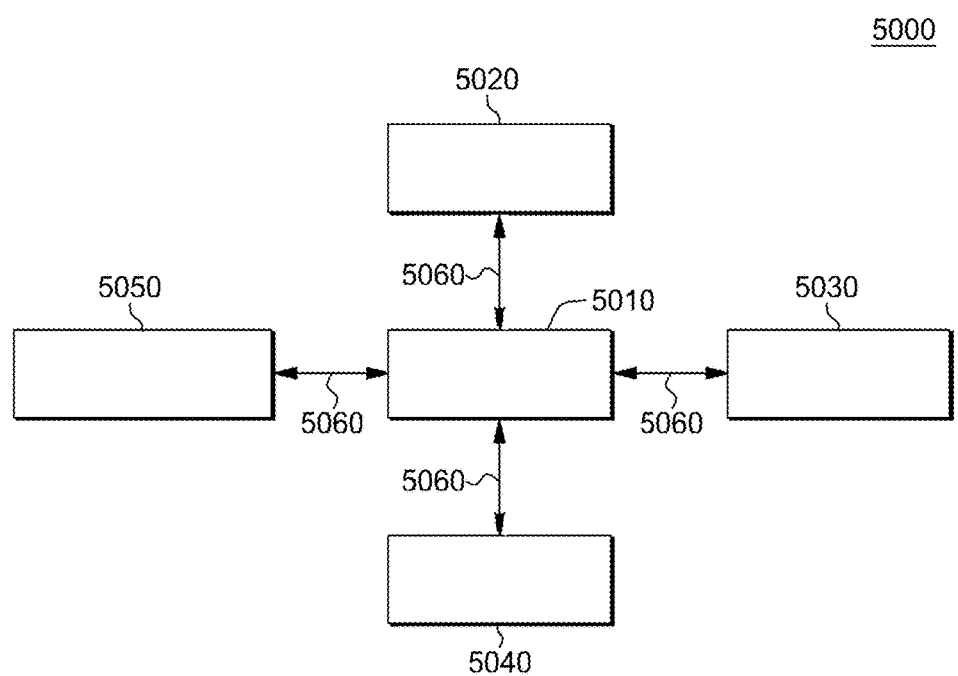
FIG. 5 is a block diagram of a computing system according to an exemplary embodiment of the present disclosure.

FIG. 5 is a block diagram of a computing system 5000 according to an exemplary embodiment of the present disclosure.

Referring to FIG. 5, the computing system 5000 may be used as a platform for performing (or controlling) the functions or operations described hereinabove with respect to the systems 1*a*, 2, and 3 of FIGS. 1A, 3, and 4 and/or the method of FIGS. 2A to 2D.

In addition, the computing system 5000 may be implemented with an UMPC, a net-book, a PDA, a portable computer (PC), a web tablet, a wireless phone, a mobile phone, a smart phone, an e-book, a PMP, a portable game console, a navigation device, a black box, a digital camera, a DMB player, a digital audio recorder, a digital audio player, a digital picture recorder, a digital picture player, a digital video recorder, a digital video player, or the like.

Referring to FIG. 5, the computing system 5000 may include a processor 5010, I/O devices 5020, a memory system 5030, a display device 5040, and a network adaptor 5050.

The processor 5010 may drive the I/O devices 5020, the memory system 5030, the display device 5040, and the network adaptor 5050 through a bus 5060.

The computing system 5000 may include a program module (not shown) for performing (or controlling) the functions or operations described hereinabove with respect to the systems 1*a*, 2, and 3 of FIGS. 1A, 3, and 4 and/or the method of FIGS. 2A to 2D according to exemplary embodiments. For example, the program module may include routines, programs, objects, components, logic, data structures, or the like, for performing particular tasks or implement particular abstract data types. The processor (e.g., 5010) of the computing system 5000 may execute instructions written in the program module to perform (or control) the functions or operations described hereinabove with respect to the systems 1*a*, 2, and 3 of FIGS. 1A, 3, and 4 and/or the method of FIGS. 2A to 2D. The program module may be programmed into the integrated circuits of the processor (e.g., 5010). In an exemplary embodiment, the program module may be stored in the memory system (e.g., 5030) or in a remote computer system storage media.

The computing system 5000 may include a variety of computing system readable media. Such media may be any available media that is accessible by the computer system (e.g., 5000), and it may include both volatile and non-volatile media, removable and non-removable media.

The memory system (e.g., 5030) can include computer system readable media in the form of volatile memory, such as random access memory (RAM) and/or cache memory or others. The computer system (e.g., 5000) may further include other removable/non-removable, volatile/non-volatile computer system storage media.

The computer system (e.g., 5000) can communicate with one or more devices using the network adapter (e.g., 5050). The network adapter may support wired communications based on Internet, LAN, WAN, or the like, or wireless communications based on CDMA, GSM, wideband CDMA, CDMA-2000, TDMA, LTE, wireless LAN, Bluetooth, or the like.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++ or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiment was chosen and described in order to best explain the principles of the present disclosure and the practical application, and to enable others of ordinary skill in the art to understand the present disclosure for various embodiments with various modifications as are suited to the particular use contemplated.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A computer-implemented method for detecting an oral temperature for a human, comprising:
   capturing a thermal image for a human using a camera having a thermal image sensor;
   detecting a face region of the human from the thermal image;
   detecting a mouth region on the face region;
   comparing a temperature value on the mouth region to a reference temperature value on a first other face region;
   detecting an open mouth region on the mouth region based on a comparison result of the temperature value on the mouth region to the reference temperature value of the first other face region;
   determining whether a mouth of the human is open enough for an oral temperature to be detected; and
   computing the oral temperature based on temperature values on the mouth region and at least one other face region, responsive to the determination of the mouth being open enough for the oral temperature to be detected.

2. The computer-implemented method of claim 1, wherein the detecting an open mouth region based on a comparison result of the temperature value on the mouth region to the reference temperature value of the other face region comprises:
   detecting a first region of the mouth region, a temperature value of the first region meeting a first criterion; and
   determining the first region as the open mouth region.

3. The computer-implemented method of claim 1, wherein the first other face region comprises a cheek region of the face region, and the at least one other face region comprises at least one of an eye region and a nose region.

4. The computer-implemented method of claim 2, wherein the first criterion comprises whether the temperature value of the first region is higher than the reference temperature value of the first other face region by a predetermined value.

5. The computer-implemented method of claim 4, wherein the predetermined value ranges from 1.5 to 5.0 degrees Celsius.

6. The computer-implemented method of claim 1, wherein the determining whether a mouth of the human is open enough for an oral temperature to be detected comprises:
   determining a first size of the open mouth region and a second size of the face region;
   when a ratio of the first size to the second size is equal to or greater than a reference value, determining the mouth is open enough for the oral temperature to be detected;
   when the ratio of the first size to the second size is smaller than the reference value, determining the mouth is closed.

7. The computer-implemented method of claim 6, wherein the reference value ranges from $1/17$ to $1/10$.

8. The computer-implemented method of claim 6, wherein the first size of the open mouth region corresponds to a number of thermal image pixels within the open mouth region, and the second size of the face region corresponds to a number of thermal image pixels within the face region.

9. The computer-implemented method of claim 1, wherein the temperatures values on the open mouth region and on at least one of an eye region and a nose region comprise maximum temperatures of the respective mouth region, the eye region, and the nose region.

10. The computer-implemented method of claim 9, wherein the computing the oral temperature comprises:
    calculating the oral temperature using at least a difference between the maximum temperature on the eye region and the maximum temperature on the nose region.

11. A system for detecting an oral temperature for a human, comprising:
    a memory device storing machine executable program instructions; and
    at least one processing device coupled to the memory device, the at least one processing device configured to run the machine executable program instructions to perform:
    capturing a thermal image for a human using a camera having a thermal image sensor;
    detecting a face region of the human from the thermal image;
    detecting a mouth region on the face region;
    comparing a temperature value on the mouth region to a reference temperature value on a first other face region;
    detecting an open mouth region on the mouth region based on a comparison result of the temperature value on the mouth region to the reference temperature value of the first other face region;
    determining whether a mouth of the human is open enough for an oral temperature to be detected; and computing the oral temperature based on temperature values on the mouth region and at least one other face region, responsive to the determination of the mouth being open enough for the oral temperature to be detected.

12. The system of claim 11, wherein to detect an open mouth region based on a comparison result of the temperature value on the mouth region to the reference temperature value of the other face region, the at least one processing device is further configured to run the machine executable program instructions to perform:
    detecting a first region of the mouth region, a temperature value of the first region meeting a first criterion; and
    determining the first region as the open mouth region.

13. The system of claim 11, wherein to determine whether a mouth of the human is open enough for an oral temperature to be detected, the at least one processing device is further configured to run the machine executable program instructions to perform:
    determining a first size of the open mouth region and a second size of the face region;
    when a ratio of the first size to the second size is equal to or greater than a reference value, determining the mouth is open enough for the oral temperature to be detected;
    when the ratio of the first size to the second size is smaller than the reference value, determining the mouth is closed.

14. The system of claim 13, wherein the first size of the open mouth region corresponds to a number of thermal image pixels within the open mouth region, and the second size of the face region corresponds to a number of thermal image pixels within the face region.

15. The system of claim 11, wherein the temperatures values on the open mouth region and on at least one of an eye region and a nose region comprise maximum temperatures of the respective mouth region, the eye region, and the nose region.

16. A computer program product stored in a non-transitory computer-readable storage medium having computer readable program instructions, the computer readable program instructions read and carried out by a processing device of performing a method for detecting an oral temperature for a human,
    wherein the method comprises:
        capturing a thermal image for a human using a camera having a thermal image sensor;
        detecting a face region of the human from the thermal image;
        detecting a mouth region on the face region;
        comparing a temperature value on the mouth region to a reference temperature value on a first other face region;
        detecting an open mouth region on the mouth region based on a comparison result of the temperature value on the mouth region to the reference temperature value of the first other face region;
        determining whether a mouth of the human is open enough for an oral temperature to be detected; and
        computing the oral temperature based on temperature values on the mouth region and at least one other face region, responsive to the determination of the mouth being open enough for the oral temperature to be detected.

17. The computer product of claim 16, wherein the detecting an open mouth region based on a comparison result of the temperature value on the mouth region to the reference temperature value of the other face region comprises:
    detecting a first region of the mouth region, a temperature value of the first region meeting a first criterion; and
    determining the first region as the open mouth region.

18. The computer product of claim 16, wherein the determining whether a mouth of the human is open enough for an oral temperature to be detected comprises:
    determining a first size of the open mouth region and a second size of the face region;
    when a ratio of the first size to the second size is equal to or greater than a reference value, determining the mouth is open enough for the oral temperature to be detected;
    when the ratio of the first size to the second size is smaller than the reference value, determining the mouth is closed.

19. The computer product of claim 18, wherein the first size of the open mouth region corresponds to a number of thermal image pixels within the open mouth region, and the second size of the face region corresponds to a number of thermal image pixels within the face region.

20. The computer product of claim 16, wherein the temperatures values on the open mouth region and on at least one of an eye region and a nose region comprise maximum temperatures of the respective mouth region, the eye region, and the nose region.

* * * * *